(12) United States Patent
Donello et al.

(10) Patent No.: US 8,242,141 B2
(45) Date of Patent: Aug. 14, 2012

(54) COMPOSITIONS AND METHODS FOR TREATING SEIZURE DISORDERS

(75) Inventors: John E. Donello, Dana Point, CA (US); Lauren M. B. Luhrs, Rancho Santa Margarita, CA (US)

(73) Assignee: Allergan, Inc., Irvine, CA (US)

(*) Notice: Subject to any disclaimer, the term of this patent is extended or adjusted under 35 U.S.C. 154(b) by 0 days.

(21) Appl. No.: 12/882,904

(22) Filed: Sep. 15, 2010

(65) Prior Publication Data
US 2011/0065747 A1     Mar. 17, 2011

Related U.S. Application Data

(60) Provisional application No. 61/243,057, filed on Sep. 16, 2009, provisional application No. 61/246,226, filed on Sep. 28, 2009.

(51) Int. Cl.
*A01N 43/40*    (2006.01)
*A01N 43/36*    (2006.01)

(52) U.S. Cl. ........................... 514/336; 514/422

(58) Field of Classification Search ............ None
See application file for complete search history.

(56) References Cited

U.S. PATENT DOCUMENTS

| | | | |
|---|---|---|---|
| 7,438,927 B2 * | 10/2008 | Berner et al. ............... | 424/473 |
| 2009/0036436 A1 | 2/2009 | LeBlond et al. | |
| 2010/0093793 A1 * | 4/2010 | Donello et al. ............ | 514/314 |

FOREIGN PATENT DOCUMENTS

| | | |
|---|---|---|
| WO | 2006/081273 | 8/2006 |
| WO | 2008/011478 | 1/2008 |
| WO | WO 2008011478 A2 * | 1/2008 |
| WO | 2008/109610 | 9/2008 |
| WO | 2009/012082 | 1/2009 |
| WO | 2009/100095 | 8/2009 |

OTHER PUBLICATIONS

Rizwan et al., Effects of Gabapentin and Antidepressant Drug Combinations on Convulsions and Memory in Mice, Pol. J. Pharmacology, 2003, 55, 965-971.*
Sivaswamy et al, "Treatment of seizures in childhood", Therapy, Future Drugs, vol. 6, No. 1, pp. 41-50, Jan. 1, 2009.
Bialer et al, "Progress report on new antiepileptic drugs", Epilepsy Research, vol. 83, No. 1, pp. 1-43, Jan. 1, 2009.
Gupta et al,"Methods and considerations for experimental evaluation of antiepileptic drugs", Indian Journal of Physiology and Pharmacology, vol. 43, No. 1, pp. 25-43, Jan. 1999.
Rizwan et al, Pol. J. Pharmacol., 55(6):965-971 (2003)).
Barker, MJ, "Cognitive effects of long-term benzodiazepine use: a meta-analysis," abstract, www.ncbi.nlm.nih.gov/pubmed/14731058, CNS Drugs, 2004; 18 (1) : 37-48.
Kamboj, Sunjeev K., et al., "The effects of immediate-release morphine on cognitive functioning in patients receiving chronic opioid therapy in palliative care," PAIN 117 (2005), 388-395.
McCracken, Lance M. Ph.D., et al., "Predicting Complaints of Impaired Cognitive Functioning in Patients with Chronic Pain," Journal of Pain and Symptom Management, vol. 21, No. 5 (May 2001), 392-396.
Martin, Roy, et al., "Comparative Cognitive Effects of Carbamazepine and Gabapentin in Healthy Senior Adults,"Epilepsia, 42 (6) (2001), 764-771.
Munoz, Maria, et al., "Reports of Memory Functioning by Patients With Chronic Pain," Clin J Pain, vol. 21, No. 4, (Jul./Aug. 2005), 287-291.
Stewart, SA, "The effects of benzodiazepines on cognition," Abstract, www.ncbi.nlm.nih.gov/pubmed/15762814, J Clin Psychiatry, 2005 ; 66 Suppl 2 : 9-13.

* cited by examiner

*Primary Examiner* — Sreeni Padmanabhan
*Assistant Examiner* — Svetlana M Ivanova
(74) *Attorney, Agent, or Firm* — Krishna G. Banerjee

(57) ABSTRACT

Disclosed are methods of treating a seizure disorder by administering to a patient in need of such treatment a compound having the following formula:

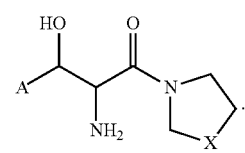

6 Claims, No Drawings

COMPOSITIONS AND METHODS FOR TREATING SEIZURE DISORDERS

CROSS REFERENCE

This application claims the benefit of U.S. Provisional Patent Application Ser. No. 61/243,057, filed on Sep. 16, 2009, and U.S. Provisional Patent Application Ser. No. 61/246,226, filed on Sep. 28, 2009, the entire disclosures of which are incorporated herein by this specific reference.

Disclosed herein is a method of treating seizure disorders by administering to a patient in need of such treatment a compound having the following formula:

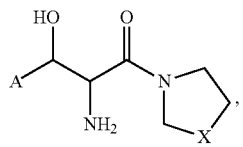

wherein X is $CH_2$ or $CH_2$—$CH_2$,
A is aryl, or is heteroaryl having 1, 2, or 3 atoms selected from the group consisting of N, S, and O,
wherein A has 0, 1, 2, or 3 substituents each comprising 0 to 8 carbon atoms, 0 to 3 oxygen atoms, 0 to 3 halogen atoms, 0 to 2 nitrogen atoms, 0 to 2 sulfur atoms, and 0 to 24 hydrogen atoms.

DETAILED DESCRIPTION OF THE INVENTION

Seizure Disorders

A seizure is an episode of abnormal motor, sensory, and/or mental functioning as the result of excessive, uncontrolled neuronal activity in the brain. Seizures may be generalized, involving both hemispheres of the brain, or partial (also called focal), involving only one hemisphere.

Generalized Seizures

Generalized seizures include infantile spasms, absence seizures, tonic-clonic seizures, atonic seizures, and myoclonic seizures. Abnormal motor function and a loss of consciousness are major features of these seizures. A patient may also experience an aura of sensory, autonomic, or psychic sensations. The aura may include paresthesia, a rising epigastric sensation, an abnormal smell, a sensation of fear, or a déjàvu sensation. A generalized seizure is often followed by a postictal state, in which a patient may sleep deeply, be confused, and/or have a headache or muscle ache. Todd's paralysis (limb weakness contralateral to the seizure focus) may be present in the postictal state.

Infantile spasms are characterized by frequent flexion and adduction of the arms and forward flexion of the trunk, usually of short duration. They occur only in the first 5 yr of life.

Typical absence seizures (also known as petit mal seizures) are characterized by a loss of consciousness with eyelid fluttering, typically for 10-30 seconds or more. There may or may not be a loss of axial muscle tone. Convulsions are absent; instead, patients abruptly stop activity, then abruptly resume it, often without realizing that a seizure has occurred. Absence seizures are genetic. They occur predominantly in children, often frequently throughout the day.

Atypical absence seizures occur as part of the Lennox-Gastaut syndrome, a severe form of epilepsy. They last longer than typical absence seizures and jerking or automatic movements are more pronounced.

Atonic seizures occur most often in children, usually as part of Lennox-Gastaut syndrome. They are characterized by a complete loss of muscle tone and consciousness.

Tonic seizures also occur most often in children, usually as part of Lennox-Gastaut syndrome. They are characterized by tonic (sustained) contraction of axial and proximal muscles, usually during sleep, and last 10 to 15 seconds. In longer tonic seizures a few, rapid clonic jerks may occur at the end of the seizure.

Tonic-clonic seizures, also known as grand mal seizures, may be primarily or secondarily generalized. A patient experiencing a primarily generalized tonic-clonic seizure will often cry out, then lose consciousness and fall. Tonic contractions then begin, followed by clonic (rapidly alternating contraction and relaxation) motion of muscles of the extremities, trunk, and head. A patient may lose urinary and fecal continence, bite his tongue, and froth at the mouth. Seizures usually last 1 to 2 min. There is no aura. Secondarily generalized tonic-clonic seizures begin with a simple partial or complex partial seizure, and then progress to a generalized seizure Myoclonic seizures are characterized by brief, rapid jerks of a limb, several limbs, or the trunk. They may be repetitive, leading to a tonic-clonic seizure. The jerks may be bilateral or unilateral. Consciousness is not lost unless the seizures progress into a generalized tonic-clonic seizure.

Juvenile myoclonic epilepsy is an epilepsy syndrome characterized by myoclonic, tonic-clonic, and absence seizures. Patients are usually adolescents. Seizures typically begin with bilateral, synchronous myoclonic jerks, followed in 90% by generalized tonic-clonic seizures. They often occur on rising in the morning. A third of patients may experience absence seizures.

Febrile seizures are associated with fever, but not intracranial infection. Benign febrile seizures are characterized by generalized tonic-clonic seizures of brief duration. Such seizures are common in children, affecting up to four percent of children younger than six years of age. Complicated febrile seizures are characterized by focal seizures lasting more than fifteen minutes or occurring more than twice in twenty four hours. Two percent of children with febrile seizures develop a subsequent seizure disorder. The risk is greater in children with complicated febrile seizures, preexisting neurologic abnormalities, onset before age 1 yr, or a family history of seizure disorders.

Status epilepticus is a seizure disorder characterized by tonic-clonic seizure activity lasting more than five to ten minutes, or two or more seizures between which patients do not fully regain consciousness. If untreated, seizures lasting more than sixty minutes may cause brain damage or death.

Complex partial status epilepticus and absence status epilepticus are characterized by prolonged episodes of mental status changes. Generalized convulsive status epilepticus may be associated with abrupt withdrawal of anticonvulsants or head trauma.

Partial Seizures

Simple partial seizures are characterized by motor, sensory, or psychomotor symptoms without loss of consciousness. Seizures in different parts of the brain often produce distinct symptoms:

TABLE 1 symptoms associated with site of seizure in the brain

| Focal Manifestation | Site of Dysfunction |
|---|---|
| Bilateral tonic posture | Frontal lobe (supplementary motor cortex) |
| Simple movements (e.g . . . , limb twitching, jacksonian march) | Contralateral frontal lobe |
| Head and eye deviation with posturing | Supplementary motor cortex |
| Abnormal taste sensation (dysgeusia) | Insula |
| Visceral or autonomic abnormalities (e.g . . . , epigastric aura, salivation) | Insular-orbital-frontal cortex |
| Olfactory hallucinations | Anteromedial temporal lobe |
| Chewing movements, salivation, speech arrest | Amygdala, opercular region |
| Complex automatic behaviorisms | Temporal lobe |
| Visual hallucinations (formed images) | Posterior temporal lobe or amygdala-hippocampus |
| Localized sensory disturbances (e.g., tingling or numbness of a limb or ½ the body) | Parietal lobe (sensory cortex) |
| Visual hallucinations (unformed images) | Occipital lobe |

An aura often precedes complex partial seizures. Patients are usually aware of their environment but may experience impaired consciousness. Patients may also experience oral automatisms (involuntary chewing or lip smacking), hand or limb automatisms (automatic purposeless movements), utterance of unintelligible sounds, tonic or dystonic posturing of the extremity contralateral to the seizure focus, head and eye deviation, usually in a direction contralateral to the seizure focus, and bicycling or pedaling movements of the legs, especially where the seizure emanates from the medial frontal or orbitofrontal head regions. Motor symptoms subside after one or two minutes, and confusion and disorientation one to two minutes later. Postictal amnesia is common.

Treatable Conditions

The compounds of the invention may be used to treat seizure disorders, that is, any condition characterized by seizures. Epilepsy is an important example of one such condition. The compounds of the invention may be used to treat epilepsy, whatever its cause, whether tumors, head trauma, central nervous system infections, medication or illicit drugs (pharmacologically-induced epilepsy), changes in hormonal cycles, or genetic, congenital, or developmental conditions. Juvenile myoclonic epilepsy, status epilepticus (complex or partial), reflex epilepsy (including primary reading epilepsy and photosensitive epilepsy), childhood absence epilepsy, and Lennox-Gastaut syndrome are examples of specific types of epilepsy that may be treated with the compounds of the invention; the compounds of the invention may be used to treat different types, as well.

The compounds of the invention may be used to treat seizures, including the generalized and partial seizures described above. Hence, examples of generalized seizures which may be treated with the compounds of the invention include infantile spasms, typical absence seizures, atypical absence seizures, atonic seizures, tonic seizures, tonic-clonic seizures, myoclonic seizures, and febrile seizures. Examples of partial seizures which may be treated with the compounds of the invention include simple partial seizures affecting the frontal lobe, contralateral frontal lobe, supplementary motor cortex, the insula, the Insular-orbital-frontal cortex, the anteromedial temporal lobe, the amygdala (including the opercular and/or other regions), the temporal lobe, the posterior temporal lobe, the amygdala, the hippocampus, the parietal lobe (including the sensory cortex and/or other regions), the occipital lobe, and/or other regions of the brain.

The compounds of the invention may also be used to treat the aura that accompanies seizures. Hence, the compounds of the invention may be used to treat the impaired consciousness, oral automatisms, hand or limb automatisms, utterance of unintelligible sounds, tonic or dystonic posturing of extremities, head and eye deviation, bicycling or pedaling movements of the legs and other symptoms that comprise the aura.

Compounds of the Invention

The method of the invention comprises administering to a patient compounds of the following formula:

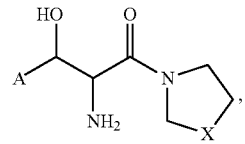

wherein X is $CH_2$ or $CH_2$—$CH_2$,

A is aryl, or is heteroaryl having 1, 2, or 3 atoms selected from the group consisting of N, S, and O, wherein A has 0, 1, 2, or 3 substituents each comprising 0 to 8 carbon atoms, 0 to 3 oxygen atoms, 0 to 3 halogen atoms, 0 to 2 nitrogen atoms, 0 to 2 sulfur atoms, and 0 to 24 hydrogen atoms.

"Aryl," as used here, means any ring or ring system that contains at least one aromatic ring, such as phenyl, naphthyl, or biphenyl. Each ring may be substituted or unsubstituted.

"Heteroaryl," as used here, means an aromatic ring or aromatic ring system in which 1, 2, or 3 of the atoms in at least one ring are N, S, or O. This includes, for example, monocyclic aryl rings wherein at least one nitrogen, oxygen, or sulfur atom is in the ring, and bicyclic aromatic ring systems wherein at least one nitrogen, oxygen, or sulfur atom is in at least one of the rings. Examples of heteroaryl include pyridinyl, furyl, thienyl, benzothienyl, benzofuryl, quinolinyl, imidazolyl, thiazolyl, oxazolyl, and the like. Each ring may be substituted or unsubstituted.

The substituents may be the same or different. Examples of substituents having the constraints defined here include, but are not limited to, the following:

hydrocarbyl, meaning a moiety consisting of carbon and hydrogen only, including, but not limited to,
  a. alkyl, meaning hydrocarbyl having no double or triple bonds, including, but not limited to,
    i) linear alkyl, e.g. methyl, ethyl, n-propyl, n-butyl, n-pentyl, n-hexyl, etc.,
    ii) branched alkyl, e.g. iso-propyl, t-butyl and other branched butyl isomers, branched pentyl isomers, etc.,
    iii) cycloalkyl, e.g. cyclopropyl, cyclobutyl, cyclopentyl, cyclohexyl, etc., which may optionally be fused to another cycloalkyl or phenyl substituent;
    iv) combinations of linear, branched, and/or cycloalkyl;

b. alkenyl, e.g. hydrocarbyl having 1 or more double bonds, including linear, branched, or cycloalkenyl;

c. alkynyl, e.g. hydrocarbyl having 1 or more triple bonds, including linear or branched (alkynyl);

d. combinations of alkyl, alkenyl, and/or akynyl;

alkyl-CN, such as —CH$_2$—CN, —(CH$_2$)$_2$—CN; —(CH$_2$)$_3$—CN, and the like;

hydroxyalkyl, i.e., alkyl-OH, such as hydroxymethyl, hydroxyethyl, and the like;

ether substituents, including —O-alkyl, alkyl-O-alkyl, and the like;

hydroxy alkyl ether, such as —COOH, thioalkyl and thioether substituents, including —S-alkyl, alkyl-S-alkyl, and the like;

amine substituents, including —NH$_2$, —NH-alkyl, —N-alkyl$^1$alkyl$^2$ (i.e., alkyl$^1$ and alkyl$^2$ are the same or different, and both are attached to N), alkyl-NH$_2$, alkyl-NH-alkyl, alkyl-N-alkyl$^1$alkyl$^2$, and the like;

aminoalkyl, meaning alkyl-amine, such as aminomethyl (—CH$_2$-amine), aminoethyl, and the like;

ester substituents, including —CO$_2$-alkyl, —CO$_2$-phenyl, etc.;

other carbonyl substituents, including aldehydes; ketones, such as acyl

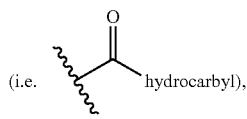

(i.e. hydrocarbyl), and the like; in particular, acetyl, propionyl, and benzoyl substituents are contemplated;

phenyl and substituted phenyl; the phenyl and substituted phenyl may itself be optionally fused with another phenyl or cycloalkyl substituent;

fluorocarbons and hydrofluorocarbons such as —CF$_3$, —CH$_2$CF$_3$, etc.;

—CN; and

—F, —Cl, —Br, or —I.

Combinations of the foregoing substituents are also possible, subject to the constraints defined.

Substituents must be sufficiently stable to be stored in a bottle at room temperature under a normal atmosphere for at least 12 hours, or stable enough to be useful for any purpose disclosed herein.

If a substituent is a salt, for example of a carboxylic acid or an amine, the counter-ion of said salt, i.e. the ion that is not covalently bonded to the remainder of the molecule is not counted for the purposes of the number of heavy atoms in a substituent. Thus, for example, the salt —CO$_2^-$Na$^+$ is a stable substituent consisting of 3 heavy atoms, i.e. sodium is not counted. In another example, the salt —NH(Me)$_2^+$Cl$^-$ is a stable substituent consisting of 3 heavy atoms, i.e. chlorine is not counted.

In one embodiment, A is pyridinyl, meaning that compounds of structures such as those shown below are contemplated. In these structures, R1, R2, and R3 are substituents as defined herein:

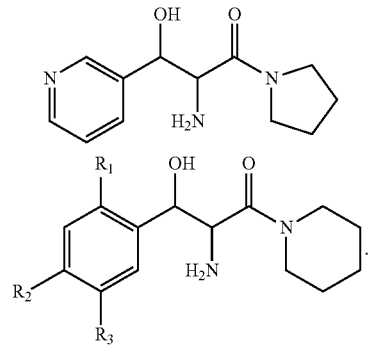

In another embodiment, A is thienyl, meaning that compounds of structures such as those shown below are contemplated. In these structures, R1 and R2 are substituents as defined herein:

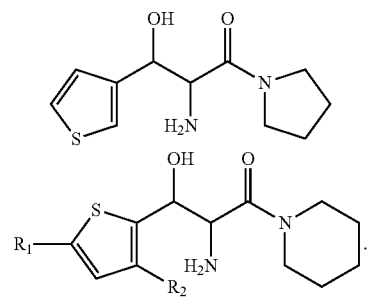

In another embodiment, A is furyl, meaning that compounds of structures such as those shown below are contemplated. In these structures, R1, R2, and R3 are substituents as defined herein:

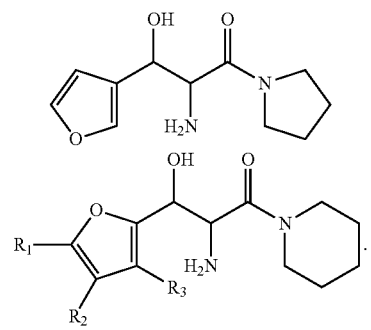

In one embodiment, each substituent is independently alkyl having from 1 to 8 carbon atoms.

In another embodiment, A is unsubstituted or has an isopropyl substituent.

In another embodiment, each substituent is —F, —Cl, —CH$_3$, or —CF$_3$.

In another embodiment, A is pyridyl, thienyl, furyl, pyrrolyl, pyrrolidinyl, imidazolyl, oxazolyl, thiazolyl, pyrazolyl, pyrimidinyl, quinolinyl, or pyrazinyl having 0, 1, 2, or 3 substituents.

Unless otherwise indicated, reference to a compound includes pharmaceutically acceptable salts, prodrugs, tautomers, alternate solid forms, and non-covalent complexes of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono, di and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Tautomers are isomers that are in rapid equilibrium with one another. They often, but do not necessarily, include a transfer of a proton, hydrogen atom, or hydride ion. For example, the structures herein are intended to include, but are not limited to, the tautomeric forms shown below:

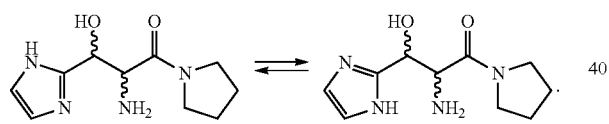

Unless stereochemistry is explicitly depicted, a structure includes every possible stereoisomer, both pure or in any possible mixture.

Alternate solid forms are different solid forms than ones that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Methods for producing the compounds of the invention are described in, for example, U.S. Patent Application Publication No. 2009/0036436, the disclosure of which is incorporated herein by reference.

Compositions useful in the method of the invention may further include an excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents.

Examples of compounds of the invention include the following

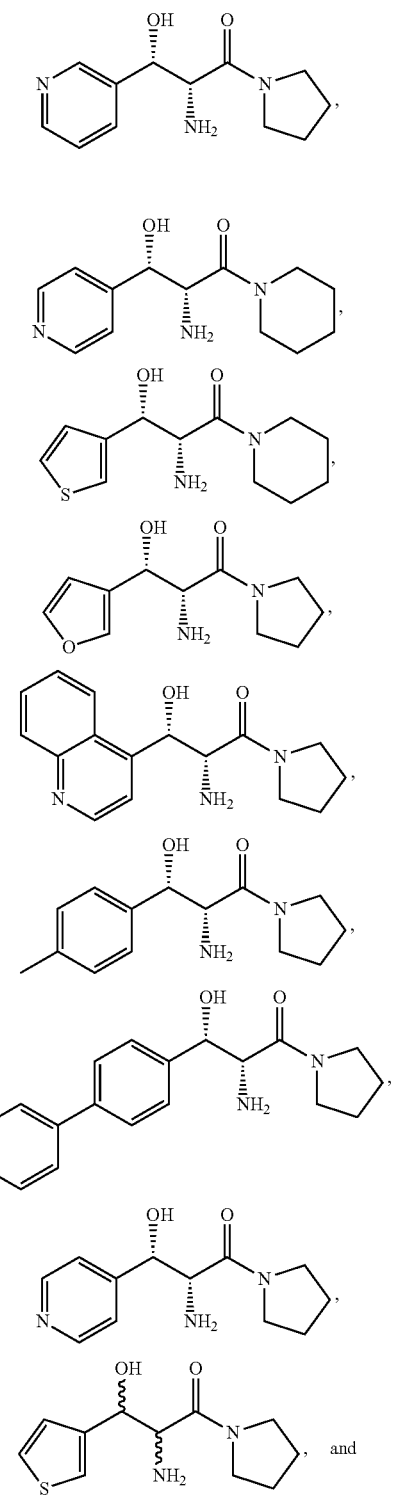

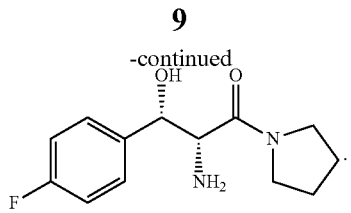

Methods of Treatment

The compounds described here may be used to treat a patient suffering from a seizure disorder.

To "treat," as used here, means to deal with medically. It includes, for example, administering a compound of the invention to prevent the onset of a seizure, to alleviate its severity, and to prevent its reoccurrence.

The compounds of the invention may be administered at pharmaceutically effective amounts. Such amounts are normally the minimum dose necessary to achieve the desired therapeutic effect; in the treatment of seizures, this amount would be roughly that necessary to reduce the frequency and/or severity of the symptoms to tolerable levels. For human adults, pharmaceutically effective amounts will generally be in the range of 1-1,000 mg/day, including 1-25 mg/day, 25-50 mg/day, 50-75 mg/day, 75-100 mg/day, 100-150 mg/day, 150-200 mg/day, 200-250 mg/day, 250-300 mg/day, 300-350 mg/day, 350-400 mg/day, 400-450 mg/day, 450-500 mg/day, 500-550 mg/day, 550-600 mg/day, 600-650 mg/day, 650-700 mg/day, 700-750 mg/day, 750-800 mg/day, 800-850 mg/day, 850-900 mg/day, 900-950 mg/day, 950-1,000 mg/day. Higher doses (1,000-3,000 mg/day) may also be effective. The actual amount of the compound to be administered in any given case will be determined by a physician taking into account the relevant circumstances, such as the severity of the seizure disorder, the age and weight of the patient, the patient's general physical condition, and the route of administration. In one embodiment, the compounds of the invention are administered at doses that are pharmaceutically effective but that do not cause sedation.

The patient may be given the compound orally in any acceptable form, such as a tablet, liquid, capsule, powder and the like. Other routes may be desirable or necessary, particularly if the patient suffers from nausea. Such other routes may include, for example, transdermal, intraperitoneal, parenteral, subcutaneous, intranasal, intrathecal, intramuscular, intravenous and intrarectal modes of delivery.

EXAMPLES

The inventors compared the anti-seizure activity of compounds of the invention against two known seizure medications, diazepam and gabapentin.

TABLE 1

Selected compounds of the invention and two known seizure medications.

| COMPOUND | STRUCTURE |
|---|---|
| Diazepam |  |
| Gabapentin | 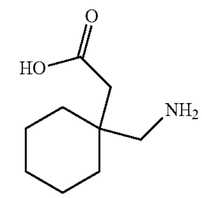 |
| A (racemate) | 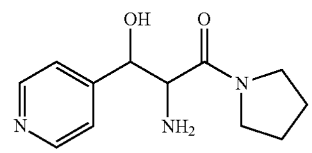 |
| B | 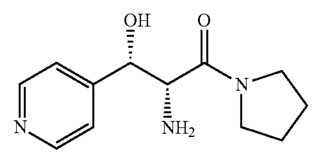 |
| C | 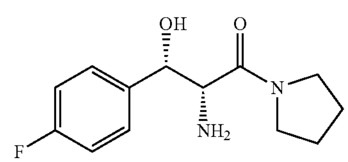 |

Male C57B/6 mice (20-25 g) were administered intraperitoneal Compound A (1 mg/kg), Compound B (1 or 10 mg/kg), Compound C (1 mg/kg), diazepam (0.5 mg/kg), gabapentin (50 mg/kg), or vehicle (ddH 2O) prior to treatment with pentylenetetrazol (PTZ, 50 mg/kg IP). Compounds A, B, C, and gabapentin were administered 60 minutes before, and diazepam or vehicle was administered 30 minutes before PTZ. Immediately following PTZ injection, mice were individually placed in an observation cage and the latency to onset of first convulsion (level 3 or higher; Table 2) was recorded, as well as the number of each type of convulsion (see Table 2 for scoring method modified from the scale used by Rizwan et al, Pol. J. Pharmacol., 55(6):965-71 (2003)).

Animals were scored for a total of 10 minutes each, and observed for an hour afterwards for signs of distress (all animals returned to normal, if slower/tired, activity levels 12-20 minutes following PTZ administration). Level 1 and 2 behaviors were not considered convulsions, but were scored to keep track of any possible sedative or abnormal effect following drug treatment. There were no differences among groups on these scores and this data is therefore not included in the convulsion analysis.

TABLE 2

PTZ scoring system

| SCORE | BEHAVIOR OBSERVED |
|---|---|
| 0 | No Change |
| 1 | Immobile, staring |
| 2 | Chewing, scratching |
| 3 | Rigid posture, tail extension |
| 4 | Single myoclonic jerk/twitch |
| 5 | Clonic convulsion involving head and/or forelimbs |
| 6 | Tonic phase, prolonged clonus |
| 7 | Tonic phase, wild running, clonic phasep |

Statistics

Data are expressed as the number of myoclonic convulsions (level 3+level 4 events), number of clonic convulsions (level 5 events), and number of tonic-clonic events (level 6+level 7 events; Table 3-1), as well as the latency to first convulsion onset (in seconds). The sum of each convulsion type/mouse (myclonic, clonic, or clonic-tonic) was entered into GraphPad Prism and analyzed by One-Way ANOVA with post-hoc Dunnett's Multiple Comparisons Tests relative to vehicle+PTZ. Overall significance was established when P<0.0125 (corrected for number of groups). Post-hoc comparisons were considered significant when P<0.05.

TABLE 3

Overall effects of treatment determined by one-way ANOVA.

| Compound | Dose (mg/kg) | Latency to first convulsion (seconds) | Number of events | | |
|---|---|---|---|---|---|
| | | | Myoclonic | Clonic | Tonic-Clonic |
| Vehicle | 0 | 96.12 ± 15.25 | 11.18 ± 2.02 | 5.43 ± 1.13 | 3.14 ± 0.57 |
| Diazepam | 0.5 | 546.4 ± 53.60 *** | 0.0 ± 0.0 *** | 0.0 ± 0.0 *** | 0.60 ± 0.60 *** |
| Gabapentin | 50 | 194.8 ± 30.41 | 1.20 ± 0.55 *** | 0.90 ± 0.18 ** | 0.20 ± 0.13 *** |
| A | 1 | 342.8 ± 76.7 *** | 1.40 ± 0.4 *** | 0.2 ± 0.1 ** | 0.5 ± 0.2 ** |
| B | 1 | 208.8 ± 84.29 | 0.83 ± 0.31 ** | 0.83 ± 0.17 * | 0.0 ± 0.0 ** |
| | 10 | 308.9 ± 92.55 * | 0.17 ± 0.17 ** | 0.50 ± 0.22 * | 0.33 ± 0.21 * |
| C | 1 | 367.1 ± 78.30 *** | 2.00 ± 1.02 ** | 0.10 ± 0.10 ** | 0.0 ± 0.0 *** |

Post-hoc Dunnett's Multiple Comparison tests identified differences between individual treatment groups relative to control.
*, , and * indicate P < 0.05, P < 0.01, and P < 0.001 relative to vehicle, respectively. N = 6-26/group.

What is claim is:

1. A method for treating epilepsy, the method comprising the step of administering to a patient in need of such treatment a compound having the following structure:

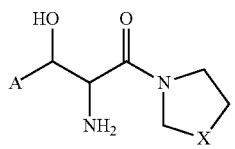

or a pharmaceutically acceptable salt thereof, wherein:
X is $CH_2$ or $CH_2$—$CH_2$,
A is aryl, or is heteroaryl having 1, 2, or 3 atoms selected from the group consisting of N, S, and O,
wherein A has 0, 1, 2, or 3 substituents each comprising 0 to 8 carbon atoms, 0 to 3 oxygen atoms, 0 to 3 halogen atoms, 0 to 2 nitrogen atoms, 0 to 2 sulfur atoms, and 0 to 24 hydrogen atoms.

2. The method of claim 1, wherein A is selected from the group consisting of pyridinyl, thienyl, furyl, quinolinyl, methylphenyl, and biphenyl.

3. The method of claim 2, wherein A is unsubstituted.

4. The method of claim 2, wherein the epilepsy is juvenile myoclonic epilepsy, complex status epilepticus, partial status epilepticus, reflex epilepsy, childhood absence epilepsy, or Lennox-Gastaut syndrome.

5. A method of treating epilepsy in a patient, comprising administering to said patient in need thereof, at least one compound selected from the group consisting of

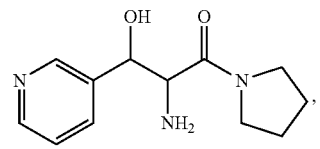

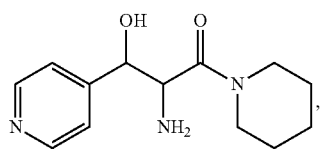

-continued

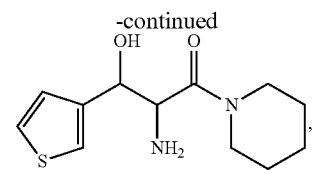

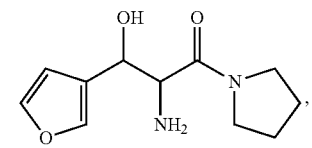

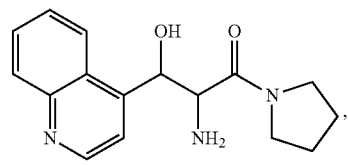

-continued
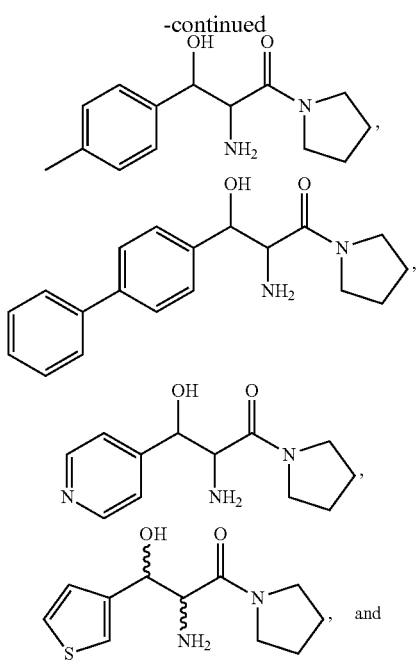
-continued
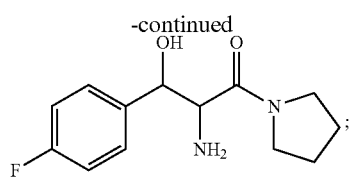
or a pharmaceutically acceptable salt thereof.
6. A method of treating epilepsy in a patient, comprising administering to said patient in need thereof, a compound of the formula
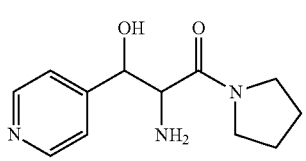
or a pharmaceutically acceptable salt thereof.
* * * * *